(12) United States Patent
Gustavsson

(10) Patent No.: US 12,730,026 B2
(45) Date of Patent: Sep. 8, 2026

(54) DETECTION SYSTEM FOR REFRIGERANT IN WATER

(71) Applicant: Siemens Energy Global GmbH & Co. KG, Munich (DE)

(72) Inventor: Peter Gustavsson, Kolmården (SE)

(73) Assignee: Siemens Energy Global GmbH & Co. KG, Munich (DE)

( * ) Notice: Subject to any disclaimer, the term of this patent is extended or adjusted under 35 U.S.C. 154(b) by 332 days.

(21) Appl. No.: 18/534,612

(22) Filed: Dec. 9, 2023

(65) Prior Publication Data

US 2024/0219087 A1 Jul. 4, 2024

(30) Foreign Application Priority Data

Dec. 29, 2022 (GB) ..................................... 2219805

(51) Int. Cl.
*G01M 3/00* (2006.01)
*G01N 33/00* (2006.01)

(52) U.S. Cl.
CPC ........... *G01M 3/00* (2013.01); *G01N 33/0011* (2013.01); *F25B 2500/222* (2013.01)

(58) Field of Classification Search
CPC .......... B01D 3/10; B01D 3/101; B01D 3/106; F25B 2500/22; F25B 2500/222; G01M 3/00; G01N 33/0011
See application file for complete search history.

(56) References Cited

U.S. PATENT DOCUMENTS 5,357,781 A * 10/1994 Tikijian ............. G01N 33/0063 73/19.1
5,693,538 A * 12/1997 Capuano ............ G01N 33/2847 73/19.1
11,473,831 B2 * 10/2022 Tsutsumi .............. F24F 13/222
12,013,163 B2 * 6/2024 Ma ........................ F25B 49/005
2020/0080918 A1 * 3/2020 Cruijff ..................... G01N 1/24
2020/0318887 A1 10/2020 Tsutsumi

FOREIGN PATENT DOCUMENTS

| | | | |
|---|---|---|---|
| CN | 104807251 | A | 7/2015 |
| JP | H0245104 | U | 3/1990 |
| JP | H11314085 | A | 11/1999 |
| JP | 2008264686 | A | 11/2008 |
| JP | 2013137142 | A | 7/2013 |
| JP | 2020510212 | A | 4/2020 |
| JP | 2022162184 | A | 10/2022 |
| WO | 2019138533 | A1 | 7/2019 |

* cited by examiner

*Primary Examiner* — Justin N Olamit
(74) *Attorney, Agent, or Firm* — Wolter Van Dyke Davis, PLLC

(57) ABSTRACT

A device and method for continuously detecting refrigerant in water, wherein the water which possibly containing refrigerant gas is fed into a vessel via a water inlet, and air is supplied to the vessel via a gas buffer, and the water is pumped out of the vessel via a pump, wherein a lower pressure is set in the vessel than in the supplied water, so that the possibly containing refrigerant gas separates from the water. Gas released from the water is fed from the vessel to a refrigerant detector, where the concentration of the refrigerant gas is measured and the gas flow exiting from the refrigerant detector is returned via a gas return line to the vessel.

19 Claims, 1 Drawing Sheet

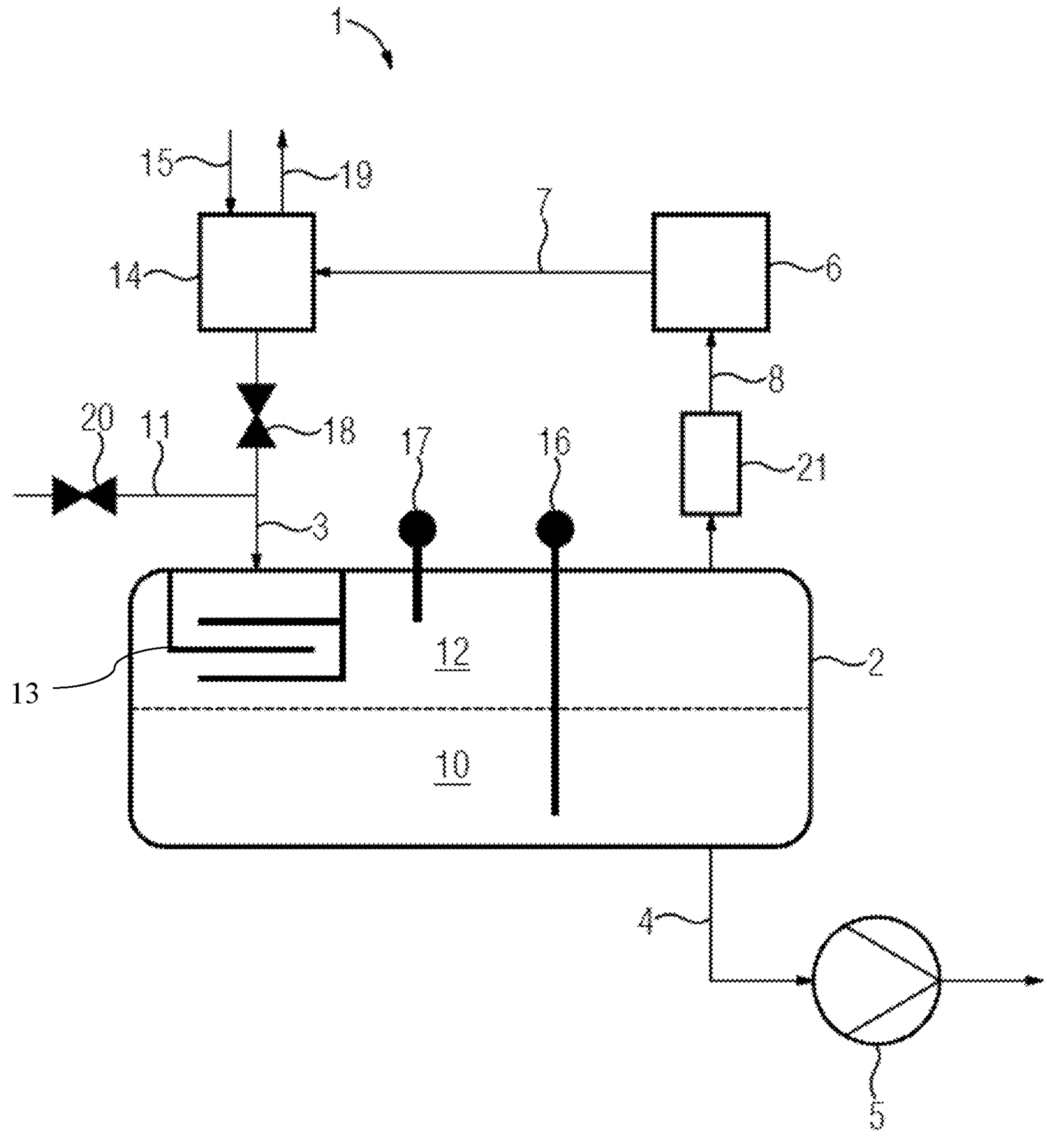
1
15
19
7
14
6
8
20
11
18
17
16
21
3
12
2
13
10
4
5

DETECTION SYSTEM FOR REFRIGERANT IN WATER

CROSS REFERENCE TO RELATED APPLICATIONS

This application claims the benefit of United Kingdom Application No. GB 2219805.5 filed 29 Dec. 2022, incorporated by reference herein in its entirety.

FIELD OF INVENTION

The invention relates to a device and a method for detecting refrigerant in water for continuous operation, especially for the use in larger heat pumps, refrigeration, and air conditioning systems where both water and refrigerant gas is used.

BACKGROUND OF INVENTION

There are commercial membrane sensors available which can detect refrigerants in water up to a concentration of 1 mg/liter. That sensor is using a membrane to separate the gas from the water. These sensors are relatively cheap but in bigger systems with large water flow, this value is not low enough to detect small leaks.

Another way to detect leaks is to drain some water over the heat exchanger and use a commercial leak detector to see if refrigerant follows the water. However, this method is manual, and the detection limit is not clear.

It is also possible to shut down the system, drain the water and allow the leaked refrigerant to accumulate in the heat exchanger for detection using a handheld device or an automatic system with a sensor that sucks air from the heat exchanger. However, this method is also manual and cannot be done while the system is in operation.

In heat pumps it is common to use a system that can detect dissolved refrigerants down to very low levels of about 0.001 mg/liter. The detection of refrigerant here is done by a Spectrophotometer, which is a very expensive gas detection device. The main disadvantage with this method is that it does not detect refrigerant bubbles, only dissolved gas since the detection point is at low points in the water line.

SUMMARY OF INVENTION

The task of the present invention is to provide a cost-effective device and method for continuous detection of refrigerant in water, particularly in larger systems with higher water flow rates such as heat pumps, and at low concentrations such as those caused by small leaks.

The task of the invention directed to an apparatus is achieved by a device for continuously detecting refrigerant gas in water according the claims. The device for continuously detecting refrigerant in water comprises a vessel having a main inlet for supplying water to the vessel, a gas buffer to supply air to the vessel, a main outlet for discharging water from the vessel, a pump connected to the main outlet for adjusting the pressure in the vessel. A lower pressure is set in the vessel than in the supplied water so that possibly containing refrigerant gas separates from the water. According to the invention a refrigerant detector for measuring the concentration of refrigerant gas is connected to the vessel, to which the gas released from the water is fed from the vessel, and the gas is returned to the vessel in a gas return line via the gas buffer as stripper gas.

The vessel is a tank which is designed for negative pressure. There is a lower pressure in the tank than in the water supplied by the water system, which causes refrigerant gas to separate from the water. To improve the amount of gas leaving the water, air is added to the water flow through a separate valve. This technology whereby a liquid is mixed with a gas to remove another gas is called stripping. The advantage of using air over other gases as stripping gas is the availability and that over time the refrigerant content does not increase.

The gas released from the water consists mainly of air and potentially leaked refrigerant gas and is sucked out of the vessel to a refrigerant detector where the concentration of the refrigerant is measured.

The outlet gas flow from the leak detector is returned to the vessel and used as the stripper gas. Only the surplus of gasses will leave the system. That surplus is formed by all gases that enter the system with the water subtracted with the gasses that leaves the system with the water again. These are the non-stripped gasses.

The invention is based on the idea that also a small leak will in this way accumulate in the tank until an equilibrium is formed between the incoming stripped gasses and the outlet surplus gas. If this equilibrium is formed at a concentration above the detection level of the detector the leak will be detected. In this way a gas detector of a more standard type and with a low cost can be used. An expensive spectral photometer for the analysis of the gas flow can be omitted.

In an advantageous embodiment of the invention the water for the continuous detections of refrigerant gas is sampled at several locations in the main water stream to be tested, to be placed at some natural and/or planned high points of the heat exchangers. The idea is to maximize the probability of catching any released refrigerant in the water.

In a further advantageous embodiment of the invention the water for the continuous detection of refrigerant gas is sampled by one or more sample lances. With that the probability of catching any released refrigerant in the water can be more increased.

In a further advantageous embodiment of the invention a ski board is inside the vessel on which the water forms a relatively thin stream so that even small gas bubbles in the water can reach the surface.

The task of the invention directed to a method is achieved by the claims and a method for continuously detecting refrigerant in water, wherein the water possibly containing refrigerant gas is fed into a vessel via a water inlet, and air is supplied to the vessel via a gas buffer, and the water is pumped out of the vessel via a pump. A lower pressure is set in the vessel than in the supplied water, so that possibly containing refrigerant gas separates from the water. According to the invention the gas released from the water is fed from the vessel to a refrigerant detector, where the concentration of the refrigerant gas is measured, and the gas is returned to the vessel in a gas return line via the gas buffer as stripper gas.

In the method for continuously detecting refrigerant gas in water, the water possibly containing refrigerant gas is fed into a vessel via a water inlet valve, and air is supplied to the vessel via a gas valve, and the water is pumped out of the vessel via a pump. A lower pressure is set in the vessel than in the supplied water, so that possibly containing refrigerant gas separates from the water. The invention is characterized in that the gas released from the water is fed from the vessel to a refrigerant detector, where the concentration of the refrigerant gas is measured and the gas flow exiting from the refrigerant detector is returned to the vessel.

The advantageous embodiments of the device apply equally to the method according to the invention.

BRIEF DESCRIPTION OF THE DRAWINGS

In the following, the invention is described in more detail with reference to a FIGURE.

FIG. 1 shows an example of a device for continuously detecting refrigerant gas in water, comprising a vessel according to the invention.

DETAILED DESCRIPTION OF INVENTION

The device 1 comprises a vessel 2 having a main inlet 3 and a main outlet 4. The main inlet 3 is for supplying water 11 via a water inlet valve 20 to the vessel 2 and the main outlet 4 for discharging water 10 from the vessel 2. A pump 5 connected to the main outlet 4 for adjusting the pressure in the vessel 2. A lower pressure is set in the vessel 2 than in the supplied water 11 so that possibly containing refrigerant gas 12 separates from the water 10 so that the refrigerant gas 12 is separated to a refrigerant side of the vessel 2 and the water 10 is separated to a water side of the vessel 2, as shown FIG. 1.

In this example, an air-gas mixture containing air at a level of 30 mg/liter is supplied to the supplied water 11 via a gas inlet valve 18. During operation 12 mg/liter is stripped-off.

According to the invention the devise comprises a detector 6 for measuring the concentration of refrigerant gas 12 which is connected to the vessel 2, to which the gas released 8 from the water 10 is fed from the vessel 2.

A detector 6 with a sensor that detects 1 ppm refrigerant gas in air, it is enough if more than 10/1000000=0.00001 ml/liter of refrigerant is stripped off in the vessel 2 for the detector 6 to detect when equilibrium is formed. If 25% of the refrigerant in the inlet is stripped in the vessel 2 the content must be 0.00004 ml/liter. Since the actual refrigerant density at normal temperature and pressure is about 5 mg/ml it means that the content must be 0.0002 mg/liter. In theory the detection level in these conditions are 0.2 microgram/liter.

For protection reasons a float valve 21 can be connected between vessel 2 and the detector 6. Via a gas return line 7 the gas flow exiting from the refrigerant detector 6 can return to the vessel 2. The gas pipe can be a metal pipe to increase the temperature and reduce the relative humidity. A gas buffer tank 14 is installed in the gas recovery line 7, to which air can be supplied and through which surplus gas 19 can be blown off. The gas 8 is returned to the vessel 2 via the gas buffer tank 14. The gas 8 is used as stripper gas.

Inside the vessel 2 a ski board 13 can be installed on which the water 10 forms a relatively thin stream so that even small gas bubbles in the water 10 can reach the surface.

During operation water containing potential leaked gas is supplied to a vessel 2 through the main inlet 3. Inside the vessel the pressure is lower than in the supplied water 11 system causing the gas 12 to separate from the water 10. To improve the amount of gas 12 that leaves the water 10, air 15 is supplied to the water stream through a valve 18.

The gas 12, which mainly contains air and potential leaked refrigerant gas, that is released from the water is sucked from the vessel 2 to a refrigerant detector 6 were the concentration of refrigerant gas is measured.

The outlet gas flow from the refrigerant detector 6 is returned to the tank and used as the stripper gas. Only the surplus of gasses will leave the system. That surplus is formed by all gases that enter the system with the water subtracted with the gasses that leaves the system with the water again.

Also a small leak will in this way accumulate in the tank until an equilibrium is formed between the incoming stripped gasses and the outlet surplus gas. If this equilibrium is formed at a concentration above the detection level of the detector the leak will be detected. In this way a gas detector of a more standard type and with a low cost can be used.

The strategic positioning of sample points 16, 17 in the main water flow is of high importance. In one embodiment of the invention, sampling lances are provided at a plurality of sampling points to be located at natural and/or designed high points of the heat exchangers. This is to maximize the likelihood that refrigerant released in the water will be captured. During operation it is also possible to alternate automatically or by command from operator between different sample points, e.g. inlet and other points. For this purpose, each sample point has a shut off valve.

With the invention it is possible to continuously and automatically operate a refrigerant detector. The invention uses air as stripping gas. Additionally, the invention allows the use of a cost-effective sensor without an expensive spectrophotometer. The invention aims to detect both bubbles and a re-presentative flow with any gas dissolved therein. Thus, the invention does not indicate the content in the water as a result, but rather the size of the leak. The invention is designed to detect gas in bubble form as well as in dissolved form.

The invention claimed is:

1. A device for continuously detecting refrigerant in water, comprising:

a vessel having a main inlet for supplying water to the vessel, a gas buffer to supply air to the vessel, a main outlet for discharging water from the vessel, a pump connected to the main outlet for adjusting a pressure in the vessel, wherein a lower pressure is set in the vessel than in the supplied water so that refrigerant gas is separated from the water, a refrigerant detector for measuring a concentration of refrigerant gas is connected to a refrigerant gas side of the vessel, wherein the main inlet is provided on the refrigerant side of the vessel, wherein the refrigerant gas separated from the water is fed from the vessel to the refrigerant detector, and wherein gas including the separated refrigerant gas is returned to the vessel in a gas return line via the gas buffer through the main inlet;

wherein a ski board is located inside the vessel on which the water forms a stream so that gas bubbles in the water can reach a surface.

2. The device according to claim 1, wherein the device is configured to sample water for continuous detection of refrigerant at several locations in the main water stream to be tested, said several locations placed at points of heat exchangers.

3. The device according to claim 1, wherein the water for the continuous detections of refrigerant gas is sampled by sample lances.

4. A method for continuously detecting refrigerant in water, comprising:

feeding water containing refrigerant gas into a vessel via a main inlet provided on a refrigerant side of the vessel, supplying air to the vessel via a gas buffer, pumping the water out of the vessel via a pump, setting a lower pressure in the vessel than in the supplied water, so that refrigerant gas is separated from the water, feeding the gas released from the water from the vessel to a refrigerant detector connected to the refrigerant side of the vessel, measuring a concentration of the refrigerant gas with the refrigerant detector, and returning the refrigerant gas separated from the water to the vessel in a gas return line via the gas buffer through the main inlet as stripper gas.

5. The method according to claim 4, wherein the water for the continuous detections of refrigerant gas is sampled at several locations in a main water stream to be tested, the several locations placed at points of heat exchangers.

6. The method according to claim 4, wherein the water for the continuous detections of refrigerant gas is sampled by sample lances.

7. The method according to claim 4, wherein a ski board is located inside the vessel on which the water forms a stream so that gas bubbles in the water can reach the surface.

8. The method of claim 4, further comprising:

forming, in the vessel, an equilibrium between the refrigerant gas returned to the vessel via the gas buffer and surplus gas blown off from the gas buffer; and accumulating a level of the refrigerant gas within the vessel based on the forming step such that the concentration of the refrigerant gas in the vessel rises above a detection level of the refrigerant detector.

9. The method of claim 8, wherein the detection level of the refrigerant detector includes 0.00001 ml/liter.

10. The method according to claim 4, wherein the setting step comprises adjusting, with the pump, the pressure in the vessel to be less than a pressure of the water supplied to the vessel through the main inlet such that the refrigerant gas is separated from the water in the vessel.

11. The method according to claim 4, wherein a detection level of the refrigerant detector is 0.0001 ml/liter.

12. The device according to claim 4, further comprising positioning a float valve between the vessel and the refrigerant detector.

13. The device of claim 4, wherein the supplying step comprises supplying, via the gas buffer, the air to the vessel through the main inlet.

14. The device of claim 13, wherein the supplying step further comprises supplying, from the gas buffer, the air to the water at the main inlet such that an air-gas mixture containing air at a level of 30 mg/liter is supplied to the vessel through the main inlet.

15. The device according to claim 1, wherein the pump is configured to adjust the pressure in the vessel to be less than a pressure of the water supplied to the vessel through the main inlet such that the refrigerant gas is separated from the water in the vessel.

16. The device according to claim 1, wherein a detection level of the refrigerant detector is 0.0001 ml/liter.

17. The device according to claim 1, further comprising a float valve positioned between the vessel and the refrigerant detector.

18. The device of claim 1, wherein the gas buffer is configured to supply the air to the vessel through the main inlet.

19. The device of claim 18, wherein the supplied air from the gas buffer is supplied to the water at the main inlet such that an air-gas mixture containing air at a level of 30 mg/liter is supplied to the vessel through the main inlet.

* * * * *